United States Patent [19]
Schenk et al.

[11] 3,979,422
[45] Sept. 7, 1976

[54] CYCLOALIPHATIC KETONES, PROCESS FOR MAKING SAME AND ODORANT AND FLAVORING COMPOSITIONS CONTAINING SAME

[75] Inventors: Hanspeter Schenk, Zumikon; Trudi Sigg-Grütter, Winterthur, both of Switzerland

[73] Assignee: Givaudan Corporation, Clifton, N.J.

[22] Filed: May 9, 1975

[21] Appl. No.: 575,907

Related U.S. Application Data

[62] Division of Ser. No. 404,582, Oct. 9, 1973, Pat. No. 3,900,520.

[30] Foreign Application Priority Data

Oct. 17, 1972   Switzerland...................... 15189/72

[52] U.S. Cl............................. 260/455 R; 426/535; 252/522

[51] Int. Cl.$^2$........................................ C07C 153/07
[58] Field of Search ................................ 260/455 R

[56] References Cited
UNITED STATES PATENTS 3,883,572    5/1975    Helmlinger et al. ............ 260/455 R

FOREIGN PATENTS OR APPLICATIONS 531,313    1/1973    Switzerland...................... 260/455 R
531,559    1/1973    Switzerland...................... 260/455 R

*Primary Examiner*—Lewis Gotts
*Assistant Examiner*—D. R. Phillips
*Attorney, Agent, or Firm*—Thomas Cifelli, Jr.

[57]    ABSTRACT

Novel cycloaliphatic ketones, a process for making them and odorant and/or flavoring compositions containing the ketones are described.

1 Claim, No Drawings

CYCLOALIPHATIC KETONES, PROCESS FOR MAKING SAME AND ODORANT AND FLAVORING COMPOSITIONS CONTAINING SAME

This is a division of application Ser. No. 404,582 filed Oct. 9, 1973, now U.S. Pat. No. 3,900,520.

FIELD OF THE INVENTION

This invention relates to the fields of new chemicals and flavorants and odorants.

SUMMARY OF THE INVENTION

The cycloaliphatic ketones provided by the present invention have the following general formula

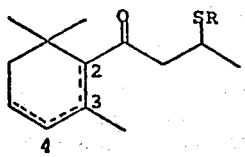

(I)

wherein R represents a hydrogen atom or the acetyl group and the broken lines denote a double-bond in the 2- or 3-position or double-bonds in each of the 2- and 4-positions.

The cycloaliphatic ketones of formula I possess particular odorant and/or flavoring properties and can accordingly be used in odorant and/or flavoring compositions, especially those having berry, fruit and/or floral notes.

As has surprisingly been found, 4-[1,1,3-trimethyl-3-cyclohexen-2-yl]-2-acetylmercapto-butanone-4 has, for example, a pronounced raspberry juice aroma with a slightly bitter after-taste. 4-[1,1,3-Trimethyl-2-cyclohexen-2-yl]-2-mercapto-butanone-4 has a fruity character with an outward-pleasing aroma reminiscent of raspberries and apricots. The fruity aroma of 4-[1,1,3-trimethyl-2-cyclohexen-2-yl]-2-acetylmercapto-butanone-4 is reminiscent of apricots and especially the slightly bitter after-taste of the green fruits. 4-[1,1,3-Trimethyl-3-cyclohexen-2-yl]-2-mercapto-butanone-4 possesses a generally fruity character with a slightly astringent acid note.

DESCRIPTION OF THE PREFERRED EMBODIMENTS

The cycloaliphatic ketones of formula I can be used in the manufacture of high-grade fruit aromas for foodstuffs (e.g. milk drinks, yogurt etc), delicacies (e.g. confectionery products such as sweets) and drinks (e.g. table water, mineral water etc) on the basis of their interesting aroma properties. Their pronounced aromatic properties allow them to be used in low concentrations; for example, in the range of 0.1–10 ppm, preferably in the range of 1–10 ppm.

For example, an addition of 5 ppm of one of the aforementioned cycloaliphatic ketones to a commercially available pineapple juice intensifies the inherent note of ripe, freshly-picked fruit in a striking manner and the astringent properties of the fruit juice are intensified.

By the addition of 5 ppm of 4-[1,1,3-trimethyl-2-cyclohexen-2-yl]-2-mercapto-butanone-4, 4-[1,1,3-trimethyl-3-cyclohexen-2-yl]-2-mercapto-butanone-4 or 4-[1,1,3-trimethyl-3-cyclohexen-2-yl]-2-acetylmercapto-butanone-4 to commercially available raspberry juices the typical flavour character of fresh, ripe raspberries is clearly intensified in these products. The addition of 2 ppm of 4-[1,1,3-trimethyl-3-cyclohexen-2-yl]-2-acetylmercapto-butanone-4 to a commercially available apricot juice intensifies its fruity note and suppresses the inherent floral note of the untreated juice in a desirable manner.

The cycloaliphatic ketones of formula I also display favourable properties in odorant compositions, for example in compositions having a floral note, in that they have the capacity to modify the fragrance of such compositions in an acceptable manner. They can accordingly also be used as odorants for the manufacture of perfumes, especially those having woody and floral notes, in which case the amount present can lie in the range of about 0.001–5 wt.%, preferably about 0.01–1 wt.%. Such odorant compositions can be used not only as actual perfumes but also as bases for the perfumery of products such as solid and liquid detergents, synthetic washing agents, aerosols and cosmetic articles of all types (e.g. soaps, lotions, creams etc). Moreover, the cycloaliphatic ketones of formula I also exhibit an excellent tenacity.

The odorant properties of individual cycloaliphatic ketones of formula I are as follows:

| | |
|---|---|
| 4-[1,1,3-trimethyl-2-cyclohexen-2-yl]-2-mercapto-butanone-4 | woody-fruity note of high intensity, reminiscent of eucalyptus and mango. |
| 4-[1,1,3-trimethyl-3-cyclohexen-2-yl]-2-mercapto-butanone-4 | fruity character with floral note, reminiscent of aniseed and apricots, slight animal note (castoreum). |
| 4-[1,1,3-trimethyl-2-cyclohexen-2-yl]-2-acetylmercapto-butanone-4 | pleasantly fruity, sweet background, reminiscent of very ripe raspberries. |
| 4-[1,1,3-trimethyl-3-cyclohexen-2-yl]-2-acetylmercapto-butanone-4 | predominant, fatty, slightly fruity, sweet note, reminiscent of ripe apricots and peaches. |

According to the process provided by the present invention, the cycloaliphatic ketones of formula I are manufactured by reacting a compound of the general formula

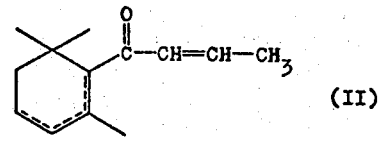

(II)

wherein the broken lines have the significance given earlier, with a compound of the general formula

HSR          (III)

wherein R has the significance given earlier, or, for the manufacture of a cycloaliphatic ketones of formula I in which R represents a hydrogen atom, replacing the acetyl group in a corresponding compound of formula I in which R represents the acetyl group by a hydrogen atom.

Cycloaliphatic ketones of the general formula

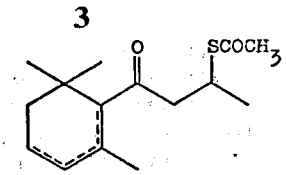

(Ia)

wherein the broken lines have the significance given earlier, can accordingly be manufactured by reacting a compound of formula II with thioacetic acid, expediently in the presence of a catalyst promoting the formation of radicals. Such catalysts are, for example, azodiisobutyronitrile, ascaridole or peroxides. The reaction can also be initiated by the action of radiation of the ultraviolet or visible region. The reaction is expediently carried out at a temperature between about 0° and 150°C (e.g. at about 100°C).

Cycloaliphatic ketones of the general formula

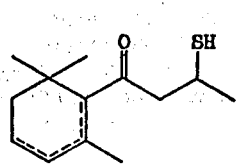

(Ib)

wherein the broken lines have the significance given earlier, can, as mentioned earlier, be manufactured either by reacting a compound of formula II with hydrogen sulphide or by cleaving an ester of formula Ia, expediently under acidic or mild alkaline conditions.

The reaction of a compound of formula II with hydrogen sulphide is expediently carried out in the presence of a base such as an alkali metal hydroxide (e.g. sodium hydroxide or potassium hydroxide), an alkaline earth metal hydroxide (e.g. calcium hydroxide), an organic base such as an amine (e.g. a dialkylamine such as diethylamine or a trialkylamine such as triethylamine) or a heterocyclic amine (e.g. piperidine). As the solvent there can be used, for example, ethanol or, especially, dimethoxyethane. The reaction can be carried out at a temperature between about 0° and 100°C, preferably at about 40°-60°C. The reaction can be carried out at normal pressure or expediently at an elevated pressure (i.e. in a closed vessel) since the reaction is accompanied by a volume reduction.

The acid cleavage of an ester of formula Ib is expediently carried out in the presence of a Lewis acid such as boron trifluoride or boron trichloride. Methanol or ether can, for example, be used as the solvent. This acid cleavage can be carried out at a temperature between about −20° and 100°C, preferably at between 10° and 50°C. The pressure is not critical, but for expedient reasons the acid cleavage is preferably carried out at normal pressure. The cleavage of the ester can also be carried out under mild alkaline conditions. Suitable bases for this purpose are alkali metal hydroxides (e.g. sodium hydroxide or potassium hydroxide), alkaline earth metal hydroxides (e.g. calcium hydroxide), alkali metal carbonates (e.g. sodium carbonate), alkali metal bicarbonates (e.g. sodium bicarbonate) and the like. As the solvent there can be used a lower alkanol (e.g. methanol or ethanol), water or mixtures thereof. The alkaline cleavage can be carried out at a temperature between about 0° and 100°C, preferably at between 40° and 60°C. The pressure is not critical, but the alkaline cleavage is preferably carried out at normal pressure.

The following Examples illustrate the process provided by the present invention:

EXAMPLE 1

1 g of 1,1,3-trimethyl-2-crotonyl-cyclohexene-3 (α-damascone) is dissolved in 2 g of thioacetic acid and the solution heated for 30 minutes at 95°C. The mixture is then cooled to room temperature and the excess thioacetic acid distilled off under a vacuum. The crude product (1.08 g) is distilled in a bulb tube. There are thus obtained 0.91 g of 4-[1,1,3-trimethyl-3-cyclohexen-2-yl]-2-acetylmercapto-butanone-4 of boiling point 98°C/0.01 mmHg.

EXAMPLE 2

1 g of 1,1,3-trimethyl-2-crotonoyl-cyclohexene-2 (β-damascone) is dissolved in 2 g of thioacetic acid and the solution heated for 60 minutes at 95°C. The mixture is then cooled to room temperature and the excess thioacetic acid distilled off under a vacuum. The crude product (1.12 g) is distilled in a bulb tube. There are thus obtained 0.89 g of 4-[1,1,3-trimethyl-2-cyclohexen-2-yl]-2-acetylmercapto-butanone-4 of boiling point 93°C/0.01 mmHg.

EXAMPLE 3

132.8 mg of 1,1,3-trimethyl-2-crotonoyl-cyclohexadiene-2,4 (damascenone) are treated with 1 ml of thioacetic acid, whereby slight warming of the mixture occurs. The solution is left to stand for 1 hour at room temperature. The excess thioacetic acid is evaporated from the mixture at 30°C/10 mmHg and the remaining residue distilled in a bulb tube. There are obtained 109 mg of 4-[1,1,3-trimethyl-2,4-cyclohexadien-2-yl]-2-acetomercapto-butanone-4 of boiling point 125°C/0.05 mmHg.

EXAMPLE 4 a. 1.5 g of 1,1,3-trimethyl-2-crotonoyl-cyclohexene-3 are added to a solution of 0.5 g of potassium hydroxide in 5 ml of absolute ethanol and the mixture is cooled to −75°C. At this temperature, 40 ml of hydrogen sulphide are condensed in. The mixture is led into a pre-cooled autoclave and this is heated for 1 hour at 50°C. The mixture is then cooled and the excess hydrogen sulphide evaporated. The mixture is taken up in ether and the ethereal solution is washed neutral with sodium chloride solution and dried over sodium sulphate. The crude 4-[1,1,3-trimethyl-3-cyclohexen-2-yl]-2-mercapto-butanone-4 remaining after distillation of the ether is distilled in a bulb tube. The boiling point of the product is 75°C/0.01 mmHg.

b. In a manner analogous to that described in part (a), from 1,1,3-trimethyl-2-crotonoyl-cyclohexene-2 there is obtained 4-[1,1,3-trimethyl-2-cyclohexen-2-yl]-2-mercapto-butanone-4 of boiling point 75°C/0.01 mmHg.

EXAMPLE 5 a. An autoclave is charged with a solution of 1 g of 1,1,3-trimethyl-2-crotonoyl-cyclohexene-3 in 20 ml of dimethoxyethane saturated with potassium hydroxide and pre-cooled to −70°C. 15 ml of hydrogen sulphide are then condensed into the solution. The autoclave is left to stand for 4 hours at 50°C and the excess hydrogen sulphide is subsequently evaporated. The product is taken up in ether, the ethereal solution washed neutral and evaporated. Distillation under a high vacuum (75°C/0.03 mmHg) gives gas chromatographically uniform 4-[1,1,3-trimethyl-3-cyclohexen-2-yl]-2-mercapto-butanone-4.

b. In a manner analogous to that described in part (a), from 1,1,3-trimethyl-2-crotonoyl-cyclohexene-2 there is obtained 4-[1,1,3-trimethyl-2-cyclohexen-2-yl]-2-mercapto-butanone-4 of boiling point 85°C/0.03 mmHg.

The following Examples illustrate compositions containing the cycloaliphatic ketones provided by the invention:

EXAMPLE A

Composition wth flowery, fresh-spicy fantasy note.

| | Parts by weight |
|---|---|
| Hyacinth synthetic | 300 |
| Pine-needle oil Sib. | 400 |
| Bornyl acetate | 100 |
| Sandela Givaudan | 30 |
| Linalol oxide | 20 |
| Orange oil Ital. | 30 |
| Hydratropaldehyde-dimethylacetal 10%* | 20 |
| Methylnonylacetaldehyde 10%* | 15 |
| C-12 aldehyde lauric 10%* | 15 |
| Oxyoctalin formate 10%* | 20 |
| Resinoide Encens 50%* | 30 |
| 4-(1,1,3-Trimethyl-3-cyclohexen-2-yl)-2-acetylthio-4-butanone 10%** | 20 |
| | 1000 |

*in diethylphthalate
**in ethyl alcohol

By the content of 4-(1,1,3-trimethyl-3-cyclohexen-2-yl)-2-acetylthio-4-butanone, there is produced a warmer, fuller note and the composition acts more powerful.

EXAMPLE B

Composition of the hyacinth type.

| | Parts by weight |
|---|---|
| Phenylethylsalicylate | 80 |
| Phenylethylisobutyrate | 80 |
| Phenylethylcinnamate | 50 |
| Phenylethylformate | 50 |
| Phenylethylalcohol | 280 |
| Cinnamic alcohol synth. | 80 |
| Phenylpropylalcohol | 50 |
| Benzyl acetate | 50 |
| Hydroxycitronellal | 100 |
| Citronellol | 50 |
| Eugenol | 30 |
| Hydratropaldehyde-dimethylacetal | 15 |
| Galbanum oil | 15 |
| Phenylacetaldehyde 50%* | 10 |
| Indol 10%* | 10 |
| Scatol 1%* | 10 |
| 4-(1,1,3-Trimethyl-2-cyclohexen-2-yl)-2-mercapto-4-butanone 10%** | 40 |
| | 1000 |

*in diethylphthalate
**in ethyl alcohol

By the content of 4-(1,1,3-trimethyl-2-cyclohexen-2-yl)-2-mercapto-4-butanone, the composition acts more natural and fuller.

What we claim is:
1. 4-[1,1,3-Trimethyl-3-cyclohexen-2-yl]-2-acetylmercapto-butanone 4.

* * * * *